United States Patent [19]
Stewart et al.

[11] Patent Number: 6,056,260
[45] Date of Patent: May 2, 2000

[54] SEAMLESS FLUID FLOW CONTROL SYSTEM

[75] Inventors: Neil G. Stewart; Gord M. Day, both of Calgary, Canada

[73] Assignee: Flexcorp, Calgary, Canada

[21] Appl. No.: 09/120,288

[22] Filed: Jul. 22, 1998

Related U.S. Application Data

[60] Provisional application No. 60/053,649, Jul. 24, 1997.

[30] Foreign Application Priority Data

Oct. 7, 1997 [CA] Canada .................................. 2217662

[51] Int. Cl.$^7$ ...................................................... F16K 7/04
[52] U.S. Cl. .................................................... 251/7; 251/4
[58] Field of Search .............................................. 251/4, 7

[56] References Cited

U.S. PATENT DOCUMENTS

| | | |
|---|---|---|
| 2,002,835 | 5/1935 | Rose . |
| 2,540,364 | 2/1951 | Adams . |
| 2,922,613 | 1/1960 | Beacham et al. ........................... 251/4 |
| 3,126,005 | 3/1964 | Smialowski . |
| 3,935,838 | 2/1976 | Beres et al. . |
| 4,091,815 | 5/1978 | Larsen ..................................... 128/325 |
| 4,354,660 | 10/1982 | Stupar et al. ............................... 251/4 |
| 5,295,825 | 3/1994 | Betush . |
| 5,407,351 | 4/1995 | Brockway . |
| 5,425,634 | 6/1995 | Brockway . |

FOREIGN PATENT DOCUMENTS

| | | |
|---|---|---|
| 060853 | 12/1983 | U.S.S.R. . |
| 890018 | 4/1959 | United Kingdom . |

*Primary Examiner*—John Fox
*Attorney, Agent, or Firm*—Gordon Freedman; Neil Teitelbaum

[57] ABSTRACT

This invention relates to a seamless system for controlling the flow of fluids, such as liquids or compressed air, through a non-fragmented length of flexible tubing. It incorporates into a single system a number of functions currently performed with separate valves within conventional dental handpiece fluid flow control units. The invention can be fitted to an existing flexible fluid supply line, within a dental delivery system without destructive insertion or removal of any intermediary parts and without contact with the fluid medium itself. The invention is conceived to accommodate from the outside, three contiguous portions (a first, an intermediate and a second portion) of a non-fragmented length of flexible tubing. It comprises a tube holder for securing the first tubing portion, a tube guide for guiding the movement of the second tubing portion relative to the first portion thereby providing selectively a folding or unfolding action to the intermediate tubing portion, so as to prevent fluid flow in said tubing by folding the intermediate portion into a closed position, or to permit flow by unfolding the intermediate portion into an open position. It further comprises actuation means for moving back and forth the second tubing portion along the tube guide.

11 Claims, 4 Drawing Sheets

SEAMLESS FLUID FLOW CONTROL SYSTEM

This application claims benefit of provisional application Ser. No. 60/053,649 filed Jul. 24, 1997.

FIELD OF THE INVENTION

This invention relates to a seamless system for controlling the flow of fluids through an uninterrupted length of flexible tubing.

BACKGROUND OF THE INVENTION

Existing dental equipment use various systems for controlling the delivery of fluid such as water or compressed air, utilizing means to pass or stop fluid flow as well as adjusting the level of fluid flow when passed through. Examples of such fluid delivery systems include, bowl rinse of water, water cup filler, flush of corrosive cleaning fluids through tubing parts, supply of air or liquid coolants to oral tools, etc. In such systems, fluid flow may be controlled by elastically manipulating a flexible tubing segment inserted in the fluid path, such as through a clamping, pinching, or folding (kinking) action to restrict or stop the flow.

As an example, U.S. Pat. No. 5,295,825 describes a control system for supplying fluids to a dental handpiece that includes a pinch valve having a flexible tubing passing the fluid supply. As with other systems using pinch valves, or clamp valves, fluid flow adjustments may not be adequately consistent for air and water due to inconsistent elastic recursion of the flexible tubing to its normal relaxed shape upon removal of the pinching action.

An example of a folding valve is that described in U.S. Pat. No. 3,395,838. There, the valve is connected at one end to a piece of tubing coming from an aerosol can, and at its opening makes direct contact with the fluid medium. Such a valve mechanism is not suitable for use in dental handpiece control equipment, as it only provides a single manual on-off control specifically dedicated for use with an aerosol can. In addition, the contact between the fluid medium and the valve itself presents other problems in dental equipment for reasons further explained below.

U.S. Pat. Nos. 5,407,351 and 5,425,634 describe an apparatus for controlling fluid delivery to a dental handpiece that includes a flexible tube valve arrangement inserted in series within the main fluid tubing via a pair of tubular fittings. Such a system requires the use of a fixed dedicated length of flex tube for its folding action. In addition, it requires two other extraneous valve arrangements for performing the fluid relay, flow adjustment and logic control functions. This makes the fluid flow system rather complicated to manufacture. Furthermore, in systems that employ seals as part of the various fittings, the seals may become contaminated thereby impeding fluid transfer. Another limitation is that the flow control valve is normally open with the risk of accidental flow of fluid upon inadvertent interruption in the pressurized pneumatic air supply for regulating the flow of fluid.

In dental equipment, the fluid delivery system is regularly cleaned by flushing the fluid path with mildly corrosive or antibacterial cleaning chemicals, such as chlorhexidine, bleach or ozone. Such chemicals may gradually corrode or contaminate metal, rubber and other corrosive non-resistant parts along the fluid path in the tubing. The more parts used on the fluid path, the greater is the risk of corrosive damage.

In view of the limitations in the prior art reviewed above, there is clearly an important need for economical fluid flow control systems that avoid any potential corrosive damage to metal valve bodies or rubber seals associated with the fluid path, by minimizing, or avoiding altogether, the utilization of such elements.

SUMMARY OF THE INVENTION

This invention incorporates into one flow control system a number of functions currently performed with separate valves within conventional dental handpiece fluid flow control units. Advantageously, it combines the functions of a relay valve, flow adjust valve, check valve and logic selector valve into a single seamless system for controlling the delivery of a fluid to a dental handpiece. The invention can be fitted to an existing flexible fluid supply line to provide means for controlling the flow of fluid such as liquids or compressed air, within a dental delivery system without destructive insertion or removal of any intermediary parts and without contact with the fluid medium itself. This would avoid problems of seal failure or contamination likely to occur in prior art systems. The invention can be configured to be in a normally closed position to prevent accidental fluid leakage upon an inadvertent system shutdown.

Accordingly, the present invention relates to a system for accommodating from the outside, three contiguous portions (a first, an intermediate and a second portion) of a non-fragmented length of flexible tubing for the purpose of controlling fluid flow in the tubing. The flow control system comprises:

(a) a tube holder for securing the first tubing portion;

(b) a tube guide for establishing a guiding path for the movement of the second tubing portion relative to the first portion thereby providing selectively a folding or unfolding action to the intermediate tubing portion, so as to prevent fluid flow in said tubing by folding the intermediate portion into a closed position, or to permit flow by unfolding the intermediate portion into an open position; and (c) actuation means for moving back and forth the second tubing portion along said path established by the tube guide.

The fluid flow control system may further comprise any of the following:

(a) flow adjustment means for limiting the degree of unfolding in the intermediate tubing portion so as to limit the rate of fluid flow therein, when said intermediate portion is in a partially open position; and/or (b) biasing spring means for allowing the tubing to remain in a normally closed position when said system is in a standby mode The actuation means can be in the form of a pneumatic cylinder enclosing a piston for being actuated within the cylinder with pressurized air applied to, or released from the cylinder, as well as coupler means for communicating the piston movement to said second portion of the tubing.

The pneumatic cylinder can be either of a single acting type with one port and a biasing spring, or of a double acting type with two ports at two opposite sides of said cylinder with or without a biasing spring. Each port is for allowing pressurized air to be either applied to, or released from the cylinder at one side thereof. With the double acting type, one port can be arranged to receive a pneumatic fluid relay signal for moving the system to an open position, and the other port for receiving a pneumatic lockout signal for locking the system in a closed position. Alternatively, the two ports can receive time-varying unbalanced pneumatic signals to allow gradual alternation of the system between open and closed positions, so as to allow timed control of the fluid flow.

BRIEF DESCRIPTION OF THE DRAWINGS

Exemplary embodiments of the invention will now be described in conjunction with the drawings in which.

DESCRIPTION OF THE INVENTION

The invention provides means for controlling the flow of fluid medium being supplied, transferred to its destination, or dumped to atmosphere or gravity drain. It can be readily fitted to existing flexible tubing in present handpiece control or any fluid delivery systems used in dental equipment. None of the invention elements needs to be in contact with fluid medium. This will provide a seamless flow control in flexible tubing for various coolants, medicants, irrigants, cleaning fluids and pressurized air required to run through a dental handpiece control system. The invention eliminates the need to insert within the fluid flow path any metal valves, rubber seals or any other elements. In this way, it avoids the problem of possible contamination or corrosive damage to vulnerable elements when using cleaners or biocides for purging fluid delivery lines including the flexible tubing.

The flow control system can be utilized with standard tubing typically used in dental equipment, such polyurethane and other kinds of flexible tubing that exhibit a self-sealing property when folded unto itself. It can also be sized to accommodate, among others, different standard tubing diameters, e.g. 0.125", 0.25" or 0.375". Some Polyurethane tubings, for example, is particularly suited for use with this invention, and offers bubble tight sealing, effective in both directions. This would eliminate the need for any additional checking mechanisms to completely stop fluid flow in the closed position. When using polyurethane tubing with the invention embodiment described below, it is found that such tubing could withstand over 475,000 folding/unfolding operations under air pressure with little or no change in its sealing and unsealing property. Pressure rating of the flow control system is equal to that of the tubing pressure rating.

Existing sources of pressurized air and other logic signals can be readily adapted to the invention. With properly controlled pneumatic signal, the flow control system will not allow fluid retraction back into the lines as is often encountered with prior art mechanical check valves. This makes the invention very suitable for use in dental and medical equipment.

Figure 1:
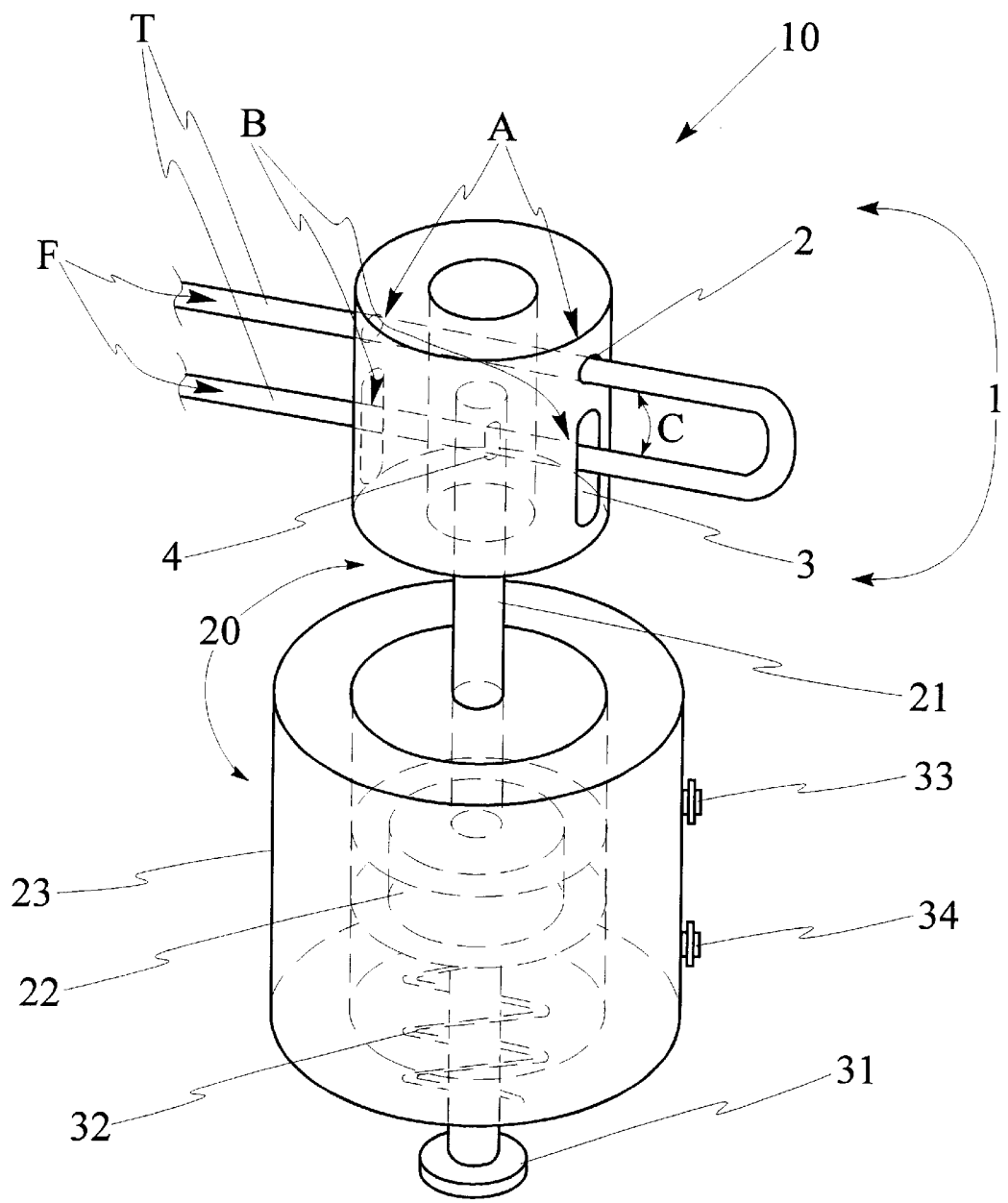
FIG. 1 is a front perspective view of a preferred embodiment of a system for controlling fluid flow in accordance with the invention, shown fitted to a continuous flexible tubing and in place for use.

In the embodiment illustrated in FIG. 1, a flow control system 10 is configured to accommodate form the outside, three contiguous portions of an non-fragmented length of flexible tubing T of a fluid delivery system (not shown). The three tubing portions are referred to as a first portion A, an intermediate portion C and a second portion B, consecutively. The flexible tubing T can be part of any fluid delivery system. The embodiment of FIG. 1 includes a cylindrical barrel 1, which incorporates a tube holder 2 and a tube guide 3. Here, the tube holder 1 is in the form of a bore cutting through the barrel 1, to serve the function of securing the first tubing portion A. The diameter of the bore 2 is so sized as to snugly retain the first tubing portion A when inserted therein. The tube guide 3 is in the form of a longitudinal slot cutting through the barrel 1, to establish a guiding path for the movement of the second tubing portion B relative to the first portion A.

The flow control system 10 is fitted to a length of tubing T by detouring a section thereof, off its way between a fluid source and a fluid destination (both not shown), without incurring any interruption in the tubing continuity. The tubing T is inserted into the tube holder 1 at its first portion A, looped back at its intermediary portion C, and inserted again into the tube guide 3. This way, the flow control system 10 is arranged to utilize the physical properties of the flexible tubing T, by being able to fold and unfold its intermediary portion C into a closed or open loop, to selectively prevent or permit fluid flow therein. The intermediary portion C is to be adjusted to proper length such that the tube is sealed when the second portion B is moved through the tube guide 3 to a position near the tube holder 1, and such that the tube is unsealed when the second portion B is moved through the tube guide 3 to a position away from the tube holder 1. Under such configuration, no break in the tubing T is required, and any contact with, or contamination by, the tubing fluid medium F is avoided.

Figure 2:
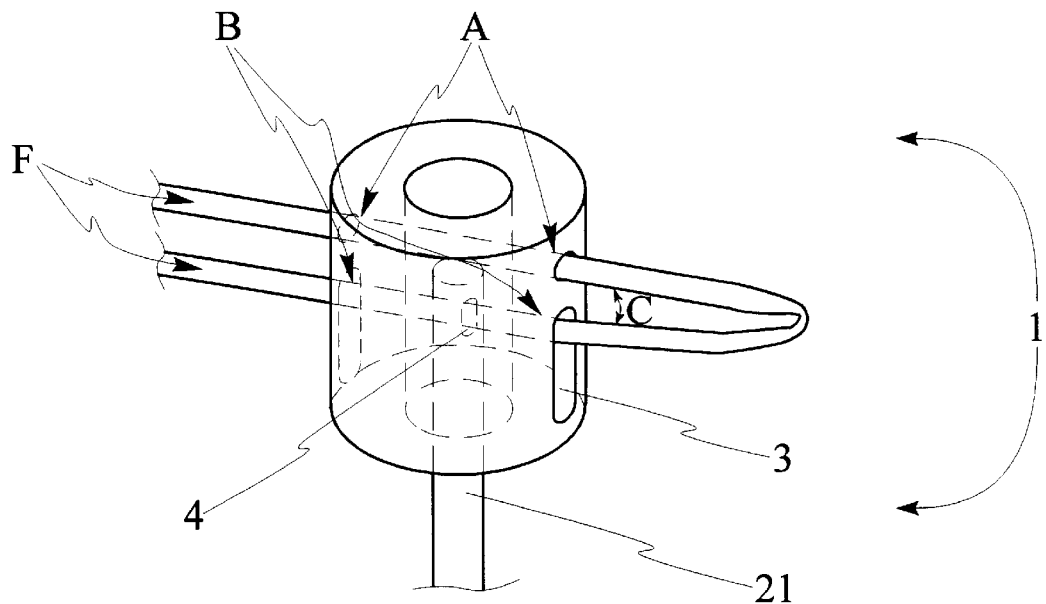
FIG. 2 is a front perspective view of the means for securing and guiding the tubing shown in a closed position, where a portion of the tubing is folded, as part of the embodiment shown in FIG. 1.
Figure 3:
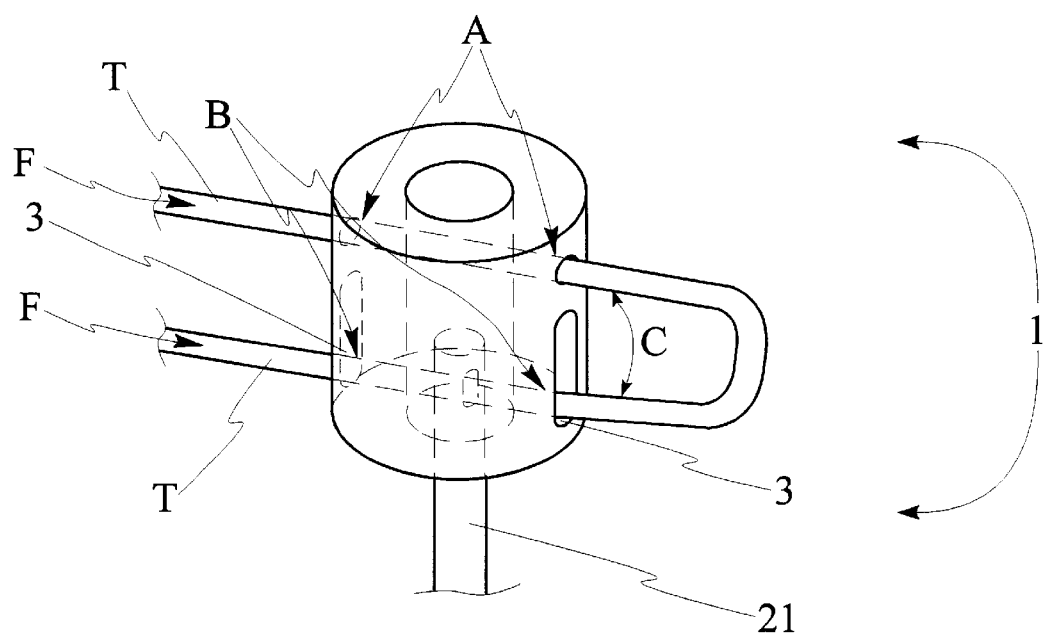
FIG. 3 is a front perspective view of the means for securing and guiding the tubing shown in an open position, where a portion of the tubing is unfolded, as part of the embodiment shown in FIG. 1.

In the embodiment of FIG. 1, the slot 3 has a width suitable for permitting the second tubing portion B to slide smoothly along the length of slot 3, when inserted therein. It also has a length axially parallel to the barrel and suitably dimensioned to allow selective movement of the flow control system 10 between a closed and a fully open position, as follows. When the second tubing portion B is moved towards the first portion A, the intermediate tubing portion C will be folded to partially prevent fluid flow, until reaching a completely closed position, as shown in FIG. 2. Alternatively, when the second tubing portion B is moved away from the first portion A, the intermediate tubing portion C will be unfolded to partially permit fluid flow, until reaching a completely open position, as shown in FIG. 3.

The cylindrical design for the flow control system 10 shown in FIG. 1 is aimed at ease of manufacturing. However, other designs are possible without affecting the function of the invention. For example, the tube holder 1 can assume other forms than a bore through a cylindrical barrel, such as a clamp, a clasp, a hook, a groove in a flat surface, etc. The tube guide 3 can also assume other forms than shown in FIG. 1, for establishing a guiding path either for a longitudinal movement (e.g. along a plane) or for an angular movement (e.g. with a pivoted mechanism). Furthermore, it is not essential to the functioning of the invention to have the tube holder 1 and the tube guide 3 as part of the same element such as the cylindrical barrel 1 shown in FIG. 1. For example, the tube holder 1 and the tube guide 3 can be in the form of two relatively movable arms.

The embodiment illustrated in FIG. 1 includes actuation means 20 for moving back and forth the second tubing portion B along the path established by the tube guide 3. In one aspect of the invention, the actuation means 20 is in the form of a pneumatic cylinder 23 which encloses a piston 22 for being actuated within the cylinder 23 with pressurized air applied thereto. The actuation means 20 further includes coupler means 22 for communicating the piston movement to the second tubing portion B which is fed through an opening 4. The coupler means 22 can be in the form of an arm connected at one end 23 to the piston 22 with a bore 4 at an end thereof. The bore 4 is sized to snugly retain the second tubing portion B when inserted therein. The arm 22 is suitably sized for smoothly fitting and axially moving inside the cylindrical barrel 1 in a proximity to the tube guide 3.

In FIG. 1, flow adjustment means 31 is provided for limiting the degree of unfolding in the intermediate tubing portion C so as to limit the rate of fluid flow therein, when said portion C is in a partially open position. The operation of the adjustment means 31 can be by a threaded mechanical travel adjustment for limiting the travel of the piston 22. This way, the degree of folding in the tubing portion C is limited and the amount of associated fluid flow is reduced accordingly.

The pneumatic cylinder 23 shown in FIG. 1 can be either single or double acting, in accordance with particular embodiments of the invention as described below.

An embodiment with a single acting pneumatic cylinder has a biasing means in the form of a spring 32 and a first port 33 for allowing pressurized air to be either applied to or released from the cylinder 23 in order to alternate the flow control system 10 between an open and a closed position. The biasing spring means 32 is provided for positioning the piston 22 and the coupler means 21 closer to the cylindrical barrel 1, so as to allow the intermediate tubing portion C to remain in a normally closed position when the flow control system 10 is in a standby mode, i.e. when no external actuating forces are applied to the actuation means 20.

Figure 4:
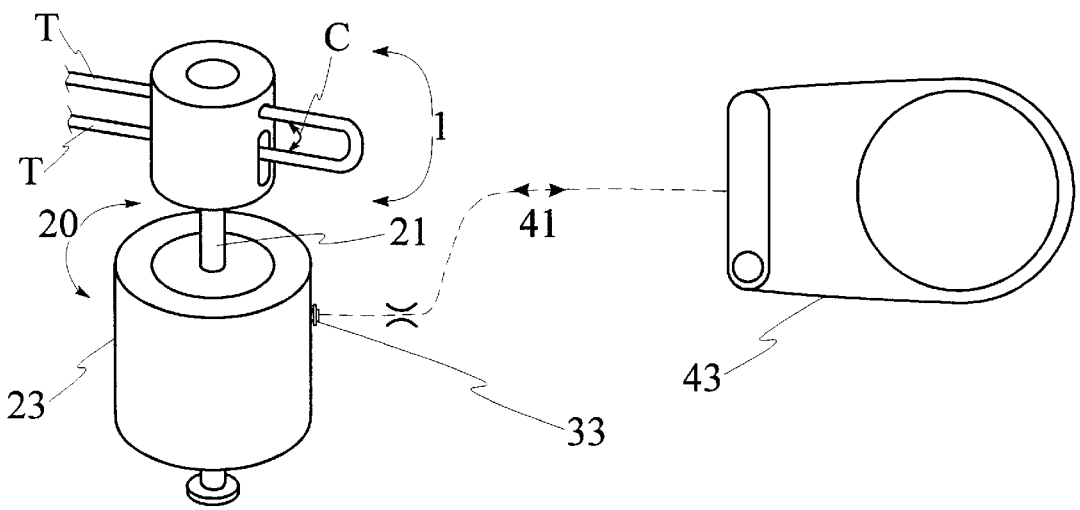
FIG. 4 is a front perspective view of one aspect of the embodiment shown in FIG. 1, where the pneumatic cylinder operates in a double acting configuration.

A single acting cylinder embodiment, as illustrated in FIG. 4, is useful when incorporating the flow control system 10 as part of a handpiece holder (not shown) in typical dental equipment. (not shown). There, a pneumatic fluid relay signal 41, in the form of pressurized air, is generated by a typical foot control device 43, to be applied to the first port 33. Such a signal will then actuate the piston and thereby move the arm 22 towards the cylindrical barrel 1, which in turn opens the fluid flow control system 10, thereby permitting fluid flow.

An alternative embodiment, with a double acting pneumatic cylinder 23, comprises a first port 33 and a second port 34 at two opposite sides of said cylinder 23, each port for allowing pneumatic signals to be applied to, or released from the cylinder 23 at one side thereof. The first port 33 is arranged for receiving a pneumatic fluid relay signal 41 for moving the fluid control system 10 to an open position, and the second port 34 is arranged for receiving a pneumatic lockout signal 42 for locking the system 10 in a closed position. A biasing spring 32 can also be provided in one aspect of this embodiment, to limit the rate of fluid flow in the flexible tubing T when being in a partially open position as explained above.

Figure 5:
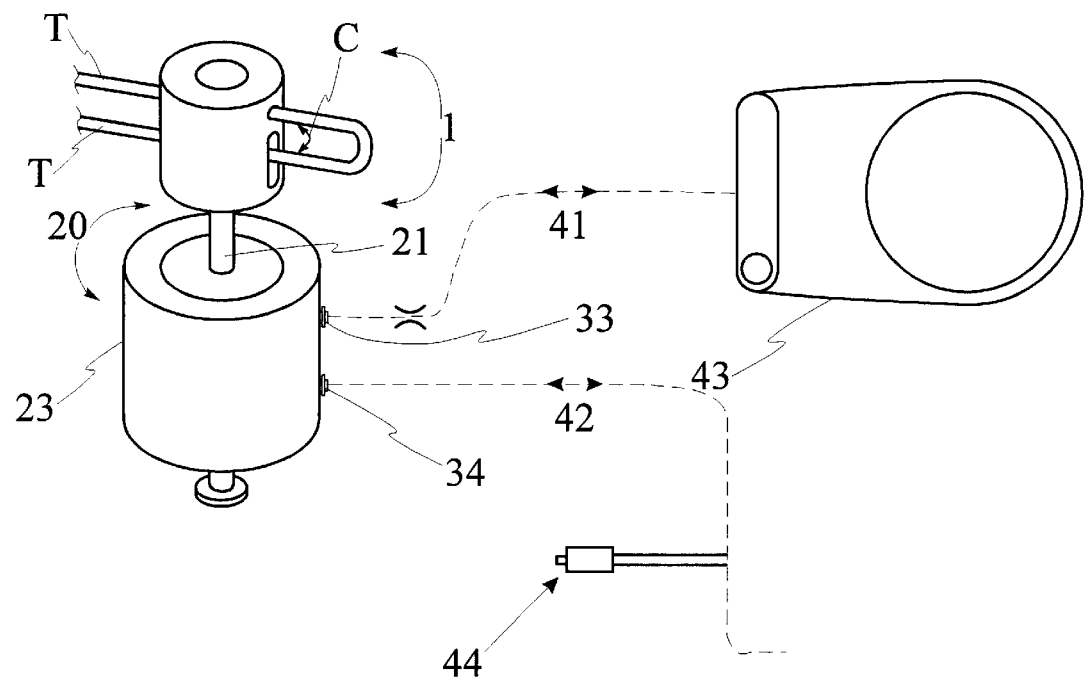
FIG. 5 is a side view of an embodiment of the invention.
Figure 6:
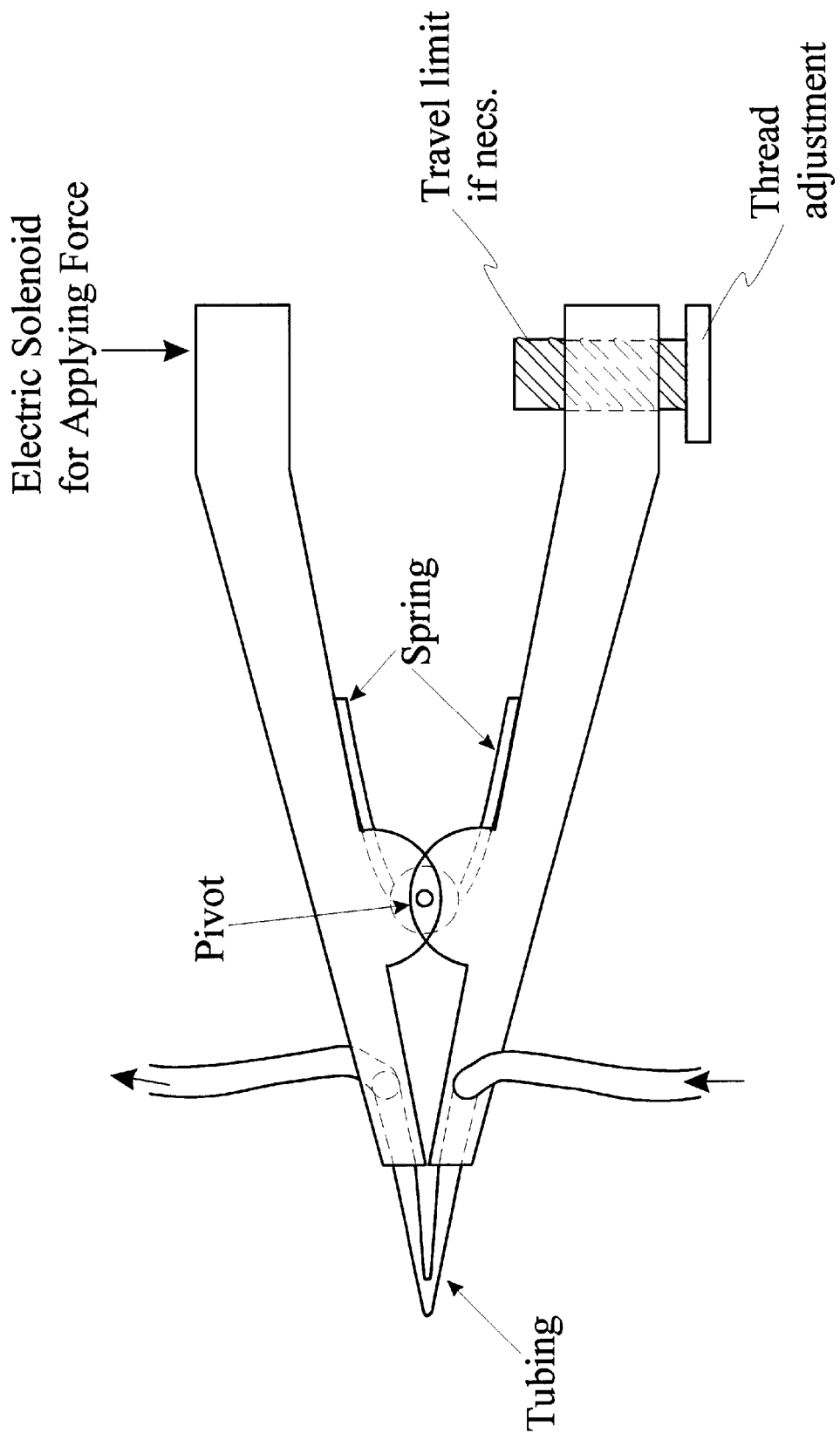
FIG. 6 is a side view of an embodiment of the invention including an electric solenoid.

An alternative embodiment having a double acting cylinder is illustrated in FIG. 5, and is useful when incorporating the flow control system 10 as part of an automatic handpiece holder (not shown) in typical dental equipment. (not shown). When the handpiece is placed in its holder, a pneumatic lockout signal 42, such as that generated by a typical auto-hangar device 44, is applied to the second port 34 to lock the system 10 in a closed position by preventing the piston 22 from being actuated to move the arm 22 away from the cylindrical barrel 1. When the handpiece is removed from its holder, air pressure is released from the second port 34, thereby leaving the system 10 still in its normally closed position, until a pneumatic fluid relay signal 41, such as that generated by a typical foot control device 43, is applied to the first port 33. Such a signal will then actuate the piston and thereby move the arm 22 away from the cylindrical barrel 1, which in turn opens the fluid flow control system 10 thereby permitting fluid flow.

With a double acting cylinder, control of the fluid flow in flexible tubing T can be either manual such as that described above, or automatically timed as described in the following. In an embodiment for timed fluid control, unbalanced pneumatic signals 41 and 42 are simultaneously applied to, or released from, the first port 33 and the second port 34. This will allow a timed movement of the system 10 from initially closed position towards an open position followed by a closed position where the force of the biasing spring prevails, thereby effecting a timed flow of fluid through the flexible tubing T.

Of course, numerous other embodiments may be envisaged, without departing from the spirit and scope of the invention.

What is claimed is:

1. A system for flow control of a fluid in a contiguous non-fragmented length of the tubing having distal from its ends a first portion, a second portion and an intermediate portion defining a contiguous non-fragmented length, the system comprising:

(a) a tube holder for securing the first tubing portion from the outside of the first tubing portion, forming part of a cylindrical barrel and comprising a second bore cutting diametrically through the barrel, said second bore being suitably sized for retaining the first tubing portion when inserted therein;

(b) a tube guide for establishing a guiding path for the movement of the second tubing portion relative to the first portion and for selectively providing a folding or unfolding action to the intermediate tubing portion, so as to prevent fluid flow in said tubing by folding the intermediate portion into a closed position, or to permit flow by unfolding the intermediate portion into an open position, forming part of a cylindrical barrel and comprising longitudinal slot cutting diametrically through the barrel, said slot having a width suitable for permitting a smooth sliding movement of the second tubing portion when inserted therein, and having a length axially parallel to the barrel and suitably dimensioned to permit the intermediate tubing portion to fold in a closed position when moved towards one end of the slot length and to unfold in a completely open position when moved towards an opposite end of said length; and an actuator for moving back and forth the second tubing portion along said path established by the tube guide comprising:
      a pneumatic cylinder enclosing a piston for being actuated within the cylinder with pressurized air applied to, or released from the cylinder, and
      coupler means for communicating the piston movement to said second portion of the tubing comprising an arm connected at one end to the piston and having at another end a first bore sized to retain said second tubing portion when inserted therein, said arm being suitably sized for smoothly fitting and axially moving inside the cylindrical barrel in a proximity to the tube guide.

2. A fluid control system as defined in claim 1, wherein the tube holder substantially encircles the outside of the first tubing portion of the contiguous non-fragmented length.

3. A fluid system as defined in claim 2 wherein the valve is normally closed.

4. A fluid control system as defined in claim 2 wherein the tube guide encircles at least a portion of the second tubing portion of the contiguous non-fragmented length.

5. A fluid flow control system as defined in claim 1 further comprising flow adjustment means for limiting the degree of unfolding in the intermediate tubing portion so as to limit the rate of fluid flow therein, when said intermediate portion is in a partially open position.

6. A fluid control system as defined in claim 1 further comprising biasing means exterior of the tubing for allowing the tubing to remain in a normally closed position when said system is in a standby mode.

7. A fluid control system as defined in claim 1 wherein the actuation means comprises an electric solenoid.

8. A fluid control system as defined in claim 1, wherein the pneumatic cylinder is of a double acting type comprising a first port a second port at two opposite sides of said cylinder, each port for allowing pressurized air to be either applied to, or released from the cylinder at one side thereof.

9. A fluid control system as defined in claim 8, wherein the first port is arranged for receiving a pneumatic fluid relay signal for moving the system to an open position, and the second port is arranged for receiving a pneumatic lockout signal for locking the system in a closed position.

10. A fluid control system as defined in claim 9, wherein the first and second ports are arranged for receiving time-varying unbalanced pneumatic signals to allow gradual alternation of the system between open and closed positions, so as to allow timed control of the fluid flow.

11. A fluid control system as defined in claim 1, wherein the pneumatic cylinder is of a single acting type comprising:

(a) biasing spring means, for positioning the piston and said coupler means relative to the tube holder so as to allow the intermediate tubing portion to remain in a normally closed position when said system is in a standby mode; and (b) a first port for allowing pressurized air to be either applied to or released from the cylinder to alternate the system between an open and a closed position.

* * * * *